United States Patent [19]

Arnaout et al.

[11] Patent Number: 5,200,319
[45] Date of Patent: * Apr. 6, 1993

[54] DIAGNOSIS OF GLOMERULONEPHRITIS

[75] Inventors: M. Amin Arnaout, Chestnut Hill; Robert T. McCluskey, Brookline; John L. Niles, Cambridge, all of Mass.

[73] Assignee: The General Hospital Corporation, Boston, Mass.

[*] Notice: The portion of the term of this patent subsequent to Feb. 25, 2009 has been disclaimed.

[21] Appl. No.: 603,782

[22] Filed: Oct. 25, 1990

Related U.S. Application Data

[63] Continuation-in-part of Ser. No. 428,286, Oct. 27, 1989, Pat. No. 5,091,303.

[51] Int. Cl.$^5$ ............... G01N 33/564; G01N 33/573; G01N 33/577
[52] U.S. Cl. .................. 435/7.24; 435/7.4; 435/23; 435/28; 435/975; 436/506; 436/518; 436/536; 436/548
[58] Field of Search ............... 435/7.24, 7.4, 23, 28, 435/975; 436/506, 518, 536, 548; 935/110

[56] References Cited

U.S. PATENT DOCUMENTS 4,452,901 6/1984 Gordon et al. ............... 436/506
4,784,942 11/1988 Harley .
5,091,303 2/1992 Arnaout et al. ............... 435/7.24

OTHER PUBLICATIONS

Van der Woude et al.; The Lancet; vol I; 425–429; 1985.
Andrassy et al.; Nephron; 49; 257–258; 1988.
Falk et al.; The New England Journal of Medicine; vol. 318; 1651–1657; 1988.
Gross et al.; The Lancet; vol. I; 1488–1489; 1987.
Goldshmeding; Kidney International; 32, 779; 1987.
Gans et al.; The Lancet; vol. I; 269–270; 1989.
Rasmussen et al.; The Lancet; vol I; 706–707; 1988.
Andrassy et al.; Clinical Nephrology; vol. 32; 159–176; 1989.
Cohen Tervaert, et al.; Kidney International; vol. 37; 799–806; 1990.
Jennette, et al.; American Journal of Pathology; vol. 135; 921–930; 1989.
Ludemann, et al.; Journal of Immunological Methods; 114; 167–174; 1988.
Nolle, et al.; Annals of Internal Medicine; vol. 111; 28–39; 1989.
Goldschmeding et al.; Kidney International; vol. 34; 558–559; 1988.
Cohen Tervaert et al.; The Lancet; vol. I; 270; 1989.
Davies et al.; British Medical Journal; 606; 1982.
Ludemann et al.; Deutsche Medizinische Wochenschrift; 113; 413–417; 1988.
Ludemann et al.; Clinical and Experimental Immunology; vol. 69; 350–357; 1987.
Parlevliet et al.; Quarterly Journal of Medicine; New Series 66; 55–63; 1988.
Hall et al.; Australian and New Zealand Journal of Medicine; vol. 14; 277–278; 1984.
Falk et al.; Kidney International; 346.
Lockwood et al.; The Lancet; vol. I; 716–719; 1987.
Johnson et al.; The Journal of Clinical Investigation; vol. 79; 1379–1387; 1987.

Primary Examiner—David Saunders
Attorney, Agent, or Firm—Fish & Richardson

[57] ABSTRACT

A purified protein (p29) capable of binding auto-antibodies present in the sera of individuals suffering from Wegener's granulomatosis. The invention also features a monoclonal antibody against the p29 protein and methods of diagnosing Wegener's granulomatosis, pauci-immune necrotizing and/or crescentic glomerulonephritis, and other conditions associated with glomerulonephritis.

9 Claims, 5 Drawing Sheets

FIG.1

| P29 | | | | | | | | | | | | | | | | | | | | | |
|---|---|---|---|---|---|---|---|---|---|---|---|---|---|---|---|---|---|---|---|---|---|
| | I | V | G | G | H | E | A | Q | P | H | S | X | P | Y | M | A | S | L | Q | M | |
| LEUKOCYTE ELASTASE | . | I | V | G | G | R | R | A | R | P | H | A | W | P | F | M | V | S | L | Q | L |
| Cathepsin G | . | . | I | . | G | G | R | E | S | R | P | H | S | R | P | Y | M | A | Y | L | Q | I |
| COMPLEMENT FACTOR D | I | L | G | G | R | E | A | E | A | H | A | R | P | Y | M | A | S | V | Q | L |
| TRYPSIN | . | . | I | V | G | G | Y | T | C | G | A | N | T | V | P | Y | Q | V | S | L | N | S |
| CHYMOTRYPSIN | . | . | I | V | N | G | E | E | A | V | P | G | S | W | P | W | Q | V | S | L | Q | D |
| PLASMIN | . | V | V | G | G | C | V | A | H | P | H | S | W | P | W | Q | V | S | L | R | T |
| COAGULATION FACTOR Xa | I | V | G | G | R | D | C | A | E | G | E | C | P | W | Q | A | L | L | V | N |
| THROMBIN | . | . | I | V | E | G | S | N | A | E | I | G | M | S | P | W | Q | V | M | L | F | R |

I=Ile; V=Val; G=Gly; H=His; E=Glu; A=Ala; Q=Gln; P=Pro; S=Ser; X=unknown;

Y=Tyr; M=Met; L=Leu.

DIAGNOSIS OF GLOMERULONEPHRITIS

This application is a continuation-in-part of Arnaout et al., U.S. Ser. No. 07/428,286 (filed Oct. 27, 1989) issued Feb. 25, 1992 as U.S. Pat. No. 5,091,303.

BACKGROUND OF THE INVENTION

This invention relates to the diagnosis of glomerulonephritis.

Glomerulonephritis is a renal disease characterized by bilateral inflammatory changes in the glomeruli of the kidneys. Rapidly progressive glomerulonephritis (RPGN) can be caused by any of several underlying conditions, including: necrotizing and/or crescentic glomerulonephritis with scant or no immune deposits (pauci-immune NCGN), anti-glomular basement membrane nephritis (anti-GBM nephritis), IgA nephropathy, lupus nephritis, and post-streptococcal glomerulonephritis. In addition, certain diseases other than glomerulonephritis, such as the hemolytic uremic syndrome or acute interstitial nephritis, may produce the clinical picture of RPGN. Pauci-immune NCGN can be restricted to the kidney (primary NCGN) or associated with Wegener's granulomatosis or a systemic disease often classified as microscopic polyarteritis nodosa.

Diagnosis of the condition causing RPGN is essential for the initiation of appropriate treatment to prevent or reverse deterioration of renal function. Renal biopsy has generally been considered to be the most definite diagnostic procedure in patients exhibiting RPGN. However, the procedure involved risk and sometimes fails to provide the correct diagnosis because the lesions in NCGN are often focal and can be missing from a small biopsy specimen (Madio, *Kidney Int.* 38:529, 1990). Furthermore, some cases of primary NCGN cannot be reliably classified.

Serologic tests have diagnostic value in some forms of RPGN. In particular, patients exhibiting RPGN often have circulating auto-antibodies directed against neutrophils and monocytes. The presence of these auto-antibodies, generally referred to as anti-neutrophil cytoplasm antibodies (ANCA), has been used as a diagnostic tool. ANCA are detected by means of an indirect immunofluorescence assay using ethanol fixed normal human neutrophils as a substrate.

Two staining patterns have been described: (1) cytoplasmic, and (2) nuclear or perinuclear (Andrassy et al., *Nephron* 49:257-258, 1988). The cytoplasmic pattern is detected in the majority of patients with active Wegener's granulomatosis (Van der Woude et al., *Lancet* 1:806,1985), and is occasionally found in other patients with primary NCGN or microscopic polyarteritis nodosa (Jennette et al., *Am. J. Pathol.* 135:921,1987, Cohen et al., *Kidney Int.* 37:799, 1990). The autoantigen associated with the cytoplasmic staining pattern is a soluble protein of 27-29 kilodalton (kD) localized to the primary or secondary granule fractions (Gross et al., *Lancet* 1:1488, 1987; Goldschmeding, *Kidney Int.* 32:779, 1987). In contrast, the nuclear or perinuclear staining pattern is seen in only a very small percentage of patients diagnosed as having Wegener's granulomatosis. This pattern, which often results from antibodies against myeloperoxidase (MPO), an antigen that is artificially redistributed in the preparation of neutrophils (Falk et al., *N. Eng. J. Med.* 318:1651), is found in some patients with primary NCGN or microscopic polyarteritis nodosa (Andrassy et al., *Clin. Nephrol.* 32:159, 1989; Gans et al., *Lancet* 1:269, 1989). Because of these distinct staining patterns the indirect immunofluorescence assay can be a useful diagnostic tool. However, analysis of the staining patterns is difficult, and it has been recommended that at least 1000 sera samples be examined before an individual is qualified to interpret the staining patterns (Rasmussen et al., *Lancet* 1:706, 1988). A simpler and more readily quantifiable assay for the auto-antibodies associated with these conditions would allow earlier and more accurate diagnosis, and would facilitate early therapeutic intervention. Accurate diagnosis is particularly important because the treatment of these disorders involves potentially toxic drugs, and clinicians may be reluctant to proceed without a definite diagnosis. More accurate diagnosis may also provide data that will contribute to an understanding of the pathogenesis of these apparently related diseases.

SUMMARY OF THE INVENTION

In general, the invention features a substantially pure protein (p29) which can be isolated from human neutrophils. The protein has a mass of approximately 29 kD as determined by SDS-PAGE, is capable of binding diisopropylfluorophosphate, possesses a pI of approximately 9.2-9.4, is capable of binding to auto-antibodies present in the sera of individuals afflicted with Wegener's granulomatosis, and has the N-terminal amino acyl sequence Ile-Val-Gly-Gly-His-Glu-Ala-Gln-Pro-His-Ser-Arg-Pro-Tyr-Met-Ala-Ser-Leu-Gln-Met-Arg-Gly-Asn-Pro-Gly-Ser-His (SEQ. ID.:1). Substantially pure means a preparation with a purity of 95% or greater by weight, substantially free of the proteins, lipids, and carbohydrates with which the protein is naturally associated.

In another aspect, the invention features a monoclonal antibody capable of forming immune complexes with p29.

In another aspect, the invention features a method of detecting auto-antibodies diagnostic for Wegener's granulomatosis. The method includes the step of contacting a biological fluid to be tested to p29. Any immune complexes formed are detected and used as an indication of the presence of auto-antibodies diagnostic for Wegener's granulomatosis in the biological fluid.

In another aspect, the invention features a method of detecting auto-antibodies diagnostic for Wegener's granulomatosis. The method includes the following steps: (a) providing immune complexes of the monoclonal antibody of the invention and an antigen reactive with the monoclonal antibody, (b) contacting the immune complexes with a biological fluid to be tested, and (c) detecting the binding of auto-antibodies to the immune complexes as a indication of the presence of auto-antibodies diagnostic for Wegener's granulomatosis in the biological fluid.

In another aspect, the invention features a vector containing a DNA sequence encoding the p29 protein.

In another aspect, the invention features a method of detecting auto-antibodies diagnostic for pauci-immune necrotizing and/or crescentic glomerulonephritis. The method consists of: (a) contacting the biological fluid to be tested with the protein of the invention, (b) contacting the biological fluid to be tested with myeloperoxidase, and (c) detecting immune complexes formed in step (a) or step (b), formation of the immune complexes being an indication of the presence of the auto-antibodies diagnostic for pauci-immune necrotizing and/or crescentic glomerulonephritis.

In another aspect, the invention features a method of detecting auto-antibodies diagnostic for pauci-immune necrotizing and/or crescentic glomerulonephritis. The method consists of: (a) providing immune complexes of the monoclonal antibody of the invention and an antigen reactive with the monoclonal antibody, (b) providing immune complexes of myeloperoxidase and a monoclonal antibody reactive with myeloperoxidase, (c) contacting the immune complexes of step (a) with the biological fluid to be tested, (d) contacting the immune complexes of step (b) with the biological fluid to be tested, and (e) detecting the binding of auto-antibodies to the immune complexes of step (a) or (b), binding of the auto-antibodies to the immune complexes of step (a) or (b) being an indication of the presence of auto-antibodies diagnostic for pauci-immune necrotizing and/or crescentic glomerulonephritis.

In another aspect, the invention features a diagnostic kit for detection of auto-antibodies in a sample of biological fluid, the auto-antibodies being diagnostic for pauci-immune necrotizing and/or crescentic granulomatosis; the kit includes p29 protein and myeloperoxidase.

In another aspect, the invention features a diagnostic kit for detection of auto-antibodies in a sample of biological fluid, the auto-antibodies being diagnostic for pauci-immune necrotizing and/or crescentic granulomatosis; the kit includes: the protein of the invention, the monoclonal antibody of the invention, myeloperoxidase, and monoclonal antibody directed against myeloperoxidase.

In another aspect, the invention features a diagnostic kit for detection of antibodies in a sample of biological fluid, the antibodies being diagnostic of glomerulonephritis; the kit includes: the protein of the invention, myeloperoxidase, complement C3, streptococcus antigen, NC1 domain of α3 chain of type IV collagen, and DNA.

The term "pauci-immune necrotizing and/or crescentic glomerulonephritis" is meant to include Wegener's granulomatosis, microscopic polyarteritis nodosa, and primary necrotizing and/or crescentic glomerulonephritis.

The compounds and methods of the invention provide means of detecting the characteristic auto-antibodies of several conditions associated with pauci-immune NCGN (these conditions include Wegener's granulomatosis, microscopic polyarteritis nodosa, and primary NCGN) and other forms of glomerulonephritis that are specific, easily interpreted and quantitative. The usual method of detection of anti-neutrophil cytoplasmic auto-antibodies employs autoantibody staining and indirect immunofluorescence. Interpretation of immunofluorescence findings requires considerable experience and results may vary from one laboratory to another. The interpretation of results in the assays of the invention depend on methods such as conventional solid or liquid phase immunoassay. The results from these techniques are far simpler to interpret than those obtained in indirect immunofluorescence assays of the prior art, where very subtle differences in the pattern of the antibody binding to fixed cellular structures must be identified and distinguished. Furthermore, unlike indirect immunofluorescence based methods, the assays of the invention are quantitative.

Detection of these diseases by the methods of the present invention use either purified antigens that bind to the characteristic auto-antibodies of the diseases or monoclonal antibodies to those antigens. In methods where detection is based on the use of purified p29 or purified myeloperoxidase there is no danger that different batches of antigen will provide different targets for autoantibody binding, as would be seen with assays using antigen preparations of lesser purity. In methods that use monoclonal antibodies, the results are similarly specific.

Other features and advantages of the invention will be apparent from the following description of the preferred embodiments, and from the claims.

DESCRIPTION OF THE PREFERRED EMBODIMENTS

We turn now to a description of preferred embodiments of the invention, after first briefly describing the drawings.

Outlined below are two methods for detecting autoantibodies present in Wegener's granulomatosis. One method employs an antigen, p29, which is recognized by the auto-antibodies; the second method employs both p29 and a monoclonal antibody directed against p29 and the production of anti-p29 monoclonal antibodies are described. Also presented are two methods for detecting auto-antibodies characteristic of conditions associated with pauci-immune NCGN, including Wegener's granulomatosis, microscopic polyarteritis nodosa, or primary NCGN. The first method employs two antigens, p29 and myeloperoxidase, which are recognized by the auto-antibodies; the second method employs these two antigens as well as monoclonal antibodies specific for each of them. A method for preparing anti-myeloperoxidase monoclonal antibodies is described.

Preparation of a Monoclonal Antibody Against the 29 kD Protein

Monoclonal antibodies against the 29 kD protein were generated by immunizing 6 week old female Balb/c mice with 10 µg of neutrophil-acid extract in complete Freund's adjuvant intradermally in the lower leg.

Neutrophil-acid extracts were prepared according to Lockwood et al. (*Lancet* 1:716, 1987). Briefly, $1 \times 10^9$ cells were washed and then sonicated for 5 min in 0.2M sodium acetate buffer, pH 4.2, at 0° C. (If cells are to be labeled with diisopropylfluorophosphate, it is added at 5 mM and the cells are held on ice for 10 minutes prior to washing). After centrifugation at 20,000 g for 20 min at 4° C., the supernatant was adjusted to pH 7.4, or dialyzed against phosphate buffered saline, pH 7.4 (PBS). The concentration of protein in the sample was determined by the method of Lowry et al. (*J. Biol. Chem.* 193:265, 1951).

The popliteal lymph nodes of the injected mice were isolated after three boosts over a two-week period. The lymphocytes were fused with the NS1 mouse plasma cell line (American Type Culture Collection) as described in Kohler et al. (*Nature,* 256:495-497, 1975). After 10-14 days of growth in HAT selective culture medium, culture supernatants from hybridomas were evaluated for anti-neutrophil activity by Western blot analysis. Western blot analysis of Wegener's granulomatosis auto-antibodies was performed as follows. The acid extract, prepared as described above (25 μg/lane), was separated by electrophoresis on sodium dodecyl sulfate polyacrylamide gels (SDS-PAGE) as described in Laemmli (*Nature* 27:680, 1970). Proteins from unstained gels were transferred electrophoretically onto nitrocellulose membranes by the method of Towbin et al. (*Proc. Natl. Acad. Sci. USA* 76:4350, 1979). The membranes were cut into strips and stained with patients' sera (1:10 dilution) followed by biotinylated secondary antibody and formation of an avidin-biotin-peroxidase complex. The bound antibodies were detected by the chromagen 3-amino-9 ethylcarbazole as a substrate for peroxidase. Monoclonal antibodies that stained a 29 kD band (p29) which co-migrated with the band identified by Wegener's granulomatosis auto-antibodies (from sera) were selected. Hybridomas with the desired activity were subcloned twice and one monoclonal antibody (mAb), 1E8, was successfully isolated.

Characterization of 1E8, a Monoclonal Anti-p29 Antibody

The mAb, 1E8, reacted with a neutrophil-derived 29 kD band on Western blots and produced an indirect immunofluorescent-staining pattern identical to that of auto-antibodies from patients' sera.

Indirect immunofluorescence analysis was performed as follows. Anti-neutrophil cytoplasmic antibodies were detected by indirect immunofluorescence using cytocentrifuged and ethanol-fixed neutrophils from normal individuals. Neutrophils were isolated by centrifugation on Ficoll-Hypaque gradients (Pharmacia, Piscataway, N.J.), followed by hypotonic lysis as described by Boyum (*Scand. J. Clin. Lab. Invest.* 97:77, 1968). Cytocentrifuge preparations were made using a Shandon Southern cytocentrifuge (Cheshire, England). Each preparation was fixed for five minutes in 100% ethanol, dried, then incubated for one hour at room temperature (RT) with serum (1:16 dilution). After two washes, the cells were stained with fluoresceinated goat anti-human Ig (Meloy, Springfield, Va.) for 60 minutes at RT, washed, and then examined using a fluorescence microscope.

Sera were obtained from ten patients diagnosed as having Wegener's granulomatosis. Clinically, all patients had upper or lower airway disease (nasal erosion, sinusitis, hemoptysis) with or without rapidly progressive renal failure. Pathologically, three patients had characteristic necrotizing granulomatous lesions in nasal biopsies. The remaining seven patients had pathologic evidence of nasal vasculitis or pulmonary capillaritis with or without necrotizing and crescentic glomerulonephritis with scanty or absent immunoglobulin deposits. Sera were also obtained from normal volunteers. All sera were frozen at −20° C. until used.

Sera from ten patients with Wegener's granulomatosis were screened for the presence of auto-antibodies reactive with normal neutrophil lysates by Western blots, as described above. All patient's sera were obtained within one month of tissue biopsy. Sera from all ten patients contained auto-antibodies against a 29 kD antigen (p29) and produced a cytoplasmic staining pattern in ethanol-fixed neutrophils. No serum from any of 200 normal individuals had anti-p29 antibodies.

Purification of p29, the 29 kD Antigen

The mAb 1E8 was utilized to affinity purify p29 using the method of Schneider et al. (*J. Biol. Chem.* 257:10766, 1982). 1E8 (of the IgG1 subclass) was bound to Sepharose-protein A beads by coupling with dimethylpimmelimidate. A 10 ml column of settled monoclonal antibody-derivatized Sepharose beads was extensively washed, then incubated with 30 mg of neutrophil-acid extract (prepared as detailed above) for three hours at RT. The column was washed with five bed-volumes of PBS followed by five-bed-volumes of PBS containing 500 mM NaCl. After reequilibration in PBS, the column was eluted with 0.2M citric acid, pH 2.75, in 1 ml fractions and neutrality was immediately established using Tris base. Eluted protein was detected spectrophotometrically at $OD_{280}$. The desired fractions were pooled and incubated with protein A-Sepharose (to remove trace amounts of contaminating mAb). Pooled fractions were concentrated and dialyzed against distilled water using collodion bags. Seven hundred μg of protein were recovered in the eluate.

Characterization of the 29 kD Antigen

Figure 1:
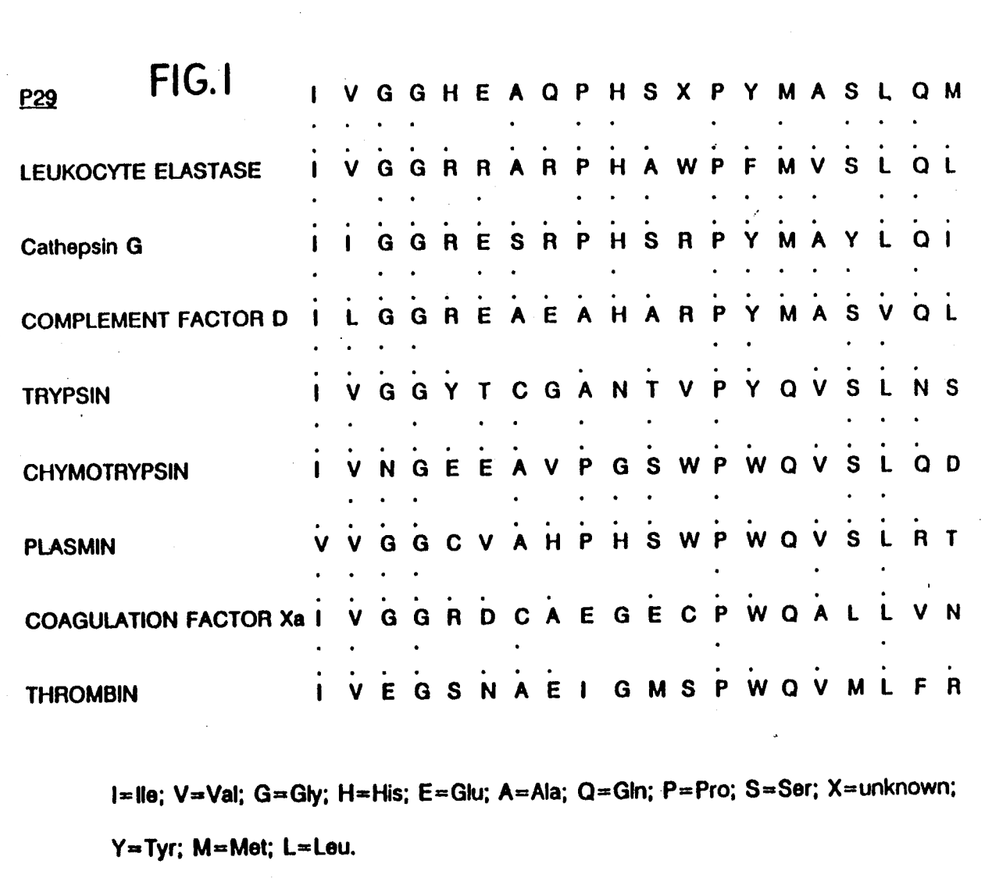
FIG. 1 is a representation of the N-terminal sequences of p29 and several serine proteases.

The affinity purified antigen recognized by 1E8 migrated on SDS-PAGE as three close bands, with the major component at 29 kD under non-reducing conditions. The purified antigen reacted with auto-antibodies from patients' sera on Western blots indicating identity between Wegener's granulomatosis autoantigen and the one recognized by 1E8. On isofocusing gels, p29 had a pI of 9.2–9.4.

p29 was shown to be a novel serine proteinase as follows. Ten μg of purified p29 were subjected to 20 cycles of Edman degradation using the Applied Biosystems Model 470 A sequenator. A single N-terminal sequence was obtained (FIG. 1) suggesting that the molecular heterogeneity of the purified protein on SDS-PAGE may reflect isoforms of one protein. Search for homologies using National Biomedical Research Foundation and Swiss protein data banks revealed that the derived sequence represents a novel protein with significant homology to the serine proteinase family. In particular, two hydrophobic residues (isoleucine and valine) are present at the N-terminus, as found at the N-termini of the catalytic chain of all serine proteinases. In addition the invariable residues glycine (at position 4) and proline (at position 13) are present in p29. p29 was clearly distinct from leukocyte elastase and cathepsin G, two neutrophil serine proteinases that are located in primary granules. p29, like leukocyte elastase and cathepsin G, also bound to radiolabelled DFP, as described below.

N-terminal sequence determination was performed as follows. One-hundred μg of purified p29 were exhaustively dialyzed against distilled water, concentrated to 200 μl and 20 μl subjected to SDS-PAGE, dry blotted onto Immobilon-P (Millipore) and stained with India ink. The major p29 band was excised with a razor blade and subjected to 20 cycles of Edman degradation using the Applied Biosystems Model 470 A sequenator. PTH derivatives were resolved by HPLC using a Cyno column (IBM) and Permaphase ETH precolumn (Applied Biosystems, Calif.), with gradient elution (solvent A:70 mM sodium acetate, pH 5.5, 5% v/v tetrahydrofuran; solvent B: acetonitrile; gradient 11–48% over 20 minutes, at a flow rate of 1 ml/minute). The N-terminal sequence obtained from the excised band was identical to that obtained from direct sequencing of the affinity purified protein.

The $^3$H-DFP binding assay was performed as follows. Monoclonal antibody 1E8 was used in a sandwich radioimmunoassay to detect binding of $^3$H-DFP to p29. A sodium sulfate cut of 1E8 ascites was diluted to 10 μg/ml in PBS and 35 μl/well were incubated for one hour at 37° C. in 96-well polyvinyl microtiter TM plate. Unoccupied binding sites were blocked with 1% nonfat dried milk. A neutrophil-acid extract, prepared without DFP as described above was diluted to 100 μg/ml and incubated with $^3$H-DFP (3.3 nM at 3 uCi/uM, NEN) for thirty minutes at RT. The extract was then added (35 ul/well) to 1E8-precoated wells or wells precoated with an irrelevant mAb or with anti-MPO mAb as controls. After a four-hour incubation period at RT, wells were washed in PBS, dried, cut and immersed in betafluor and counted in a beta counter. The tritiated DFP bound only to the wells containing mAb 1E8.

Isoelectric focusing was performed in 0.75 mm thick gels using a vertical gel apparatus (Hoeffer Scientific) and a pH range 3.5–11. Gels were run at 2.5 mA constant current for 16 hours at 4° C., fixed, stained with Coomassie Blue R-250 and destained.

Indirect Solid Phase Immunoassay for Wegener's Granulomatosis

In this assay, monoclonal anti-p29 antibodies are used to capture protein from neutrophil-acid extract; after washing the captured proteins are exposed to test sera. Retained auto-antibodies are detected with an anti-human Ig antibody conjugated to a marker.

Microtiter TM wells are pre-coated with an ammonium sulfate cut of mAb 1E8, exposed to neutrophil-acid extract (prepared as described above), and allowed to incubate for 4 hours. Wells are washed with PBS and exposed to test serum at 1:100 dilution in a total volume of 35 μl. After 60 minutes at RT the wells are washed with PBS and developed with $^{125}$I-labeled goat-anti-human Ig antibody (preabsorbed to mouse IgG). Wells are cut, dried, and counted in a gamma counter. The $^{125}$I-labeled goat-anti-human Ig antibody may be replaced with an anti-human Ig antibody conjugated to an enzyme or other radiometric or nonradiometric marker.

The assay may be provided in a convenient kit containing mAb 1E8 bound to microtiter TM wells (or a similar substrate), a positive control sample (e.g., serum from a patient positively diagnosed as having Wegener's granulomatosis), and other reagents needed to perform the assay.

Direct Solid Phase Immunoassay for Wegener's Granulomatosis

In this assay, purified p29 is used to capture auto-antibodies from test sera. The captured auto-antibodies are then detected with anti-human Ig antibody conjugated to a marker.

p29 is affinity purified from neutrophil-acid extracts as described above. Purified p29 is coated onto microtiter TM wells. Serum (35 μl of a 1:100 dilution) from a patient is added to the microtiter TM well and allowed to incubate for 60 minutes. The microtiter TM wells are washed with PBS and developed with a radiolabeled, enzyme conjugated, or otherwise labeled anti-Ig antibody.

The assay may be provided in a convenient kit containing p29 bound to microtiter TM wells (or other suitable substrates), a positive control sample (e.g., serum from a patient positively diagnosed as having Wegener's granulomatosis), and other reagents needed to perform the assay.

Production of Additional Monoclonal Antibodies Against p29 Protein

Our discovery that the circulating auto-antibodies in the serum of patients with Wegener's granulomatosis are directed against the protein we have identified, p29, makes possible the routine production of monoclonal antibodies which are specific for p29. Such antibodies can be generated according to the procedure described above, or by an even simpler procedure, as follows.

Serum derived from any patient with Wegener's granulomatosis is contacted with lysed neutrophils, and the resulting immunoprecipitate isolated; this precipitate will contain the p29 protein complexed with antibody. This immunoprecipitate is used to immunize animals, e.g., mice, many of which then produce antibodies to the p29 protein. The culture supernatants from hybridomas made based on such immunizations are then screened for those containing monoclonal antibodies which bind to lysate from normal neutrophils. Recognition of the p29 protein is confirmed by Western blotting, as described above.

Cloning of the Gene for p29

The p29 N-terminal amino acid sequence information recited above will render cloning of the gene encoding that protein routine, particularly in view of the small size of the protein. The N-terminal sequence information will be used to make synthetic oligonucleotides, which will be used to obtain cDNA encoding the p29 protein, according to standard techniques, i.e., screening of cDNA library from neutrophils.

Immunoassays for Pauci-immune NCGN Auto-antibodies

Auto-antibodies characteristic of any of the three conditions associated with pauci-immune NCGN (Wegener's granulomatosis, microscopic polyarteritis nodosa, and primary NCGN), can be detected by combining an assay for anti-p29 auto-antibodies with an assay for anti-myeloperoxidase auto-antibodies.

Preparation of MPO

Purified human polymorphonuclear leukocyte myeloperoxidase (MPO) (CalBiochem Behring; San Diego, Calif.) can be used to prepare anti-MPO antibodies as outlined above for anti-p29 monoclonal antibodies. Purified anti-MPO monoclonal antibody can be used to screen the sera of patients diagnosed as having necrotizing and/or crescentic glomerulonephritis. The majority of the sera samples which react with the chosen anti-MPO monoclonal antibody should generate a nuclear or perinuclear staining pattern in an indirect immunofluorescence assay of ethanol-fixed normal neutrophils (Van de Woude et al., supra). Hybridomas with the desired reactivity can be subcloned, and the anti-MPO monoclonal antibody can be purified by standard techniques using protein A-Sepharose chromatography. Alternatively, commercially available (Dako, Santa Barbara, Calif.) monoclonal anti-myeloperoxidase antibodies can be used.

Indirect Solid Phase Immunoassay for Pauci-immune NCGN Auto-antibodies

In this assay, monoclonal anti-p29 and anti-MPO antibodies are used to capture proteins from neutrophil-acid extract; after washing, the captured proteins are exposed to test sera. The retained auto-antibodies are detected with an anti-human Ig antibody conjugated to a marker.

Microtiter TM wells are pre-coated with an ammonium sulfate cut of mAb 1E8 or purified anti-MPO mAb, exposed to neutrophil-acid extract (prepared as described above), and allowed to incubate for 4 hours. Wells are washed with PBS and exposed to test serum at 1:100 dilution in a total volume of 35 μl. After 60 minutes at RT the wells are washed with PBS and developed with $^{125}$I-labeled goat-anti-human Ig antibody (preabsorbed to mouse IgG). Wells are cut, dried, and counted in a gamma counter. The $^{125}$I-labeled goat-anti-human Ig antibody may be replaced with an anti-human Ig antibody conjugated to an enzyme or other radiometric or nonradiometric marker.

The assay may be provided in a convenient kit containing mAb 1E8 bound to some microtiter TM wells (or a similar substrate), anti-MPO mAb bound to other microtiter TM wells (or a similar substrate), a positive control sample (e.g., serum from a patient positively diagnosed as having pauci-immune NCGN), and other reagents needed to perform the assay. Alternatively both mAbs can be placed in one well. Such a kit would allow detection of the auto-antibodies present conditions associated with pauci-immune NCGN.

Direct Solid Phase Immunoassay for NCGN Auto-antibodies

In this assay, purified p29 and purified MPO are used to capture auto-antibodies from test sera. The captures auto-antibodies are then detected with anti-human Ig antibody conjugated to a marker.

p29 is affinity purified from neutrophil-acid extracts as described above and coated onto a set of microtiter TM wells. A second microtiter TM well is coated with purified MPO. Serum (35 μl of a 1:100 dilution) from a patient is added to the microtiter TM wells and allowed to incubate for 60 minutes. The microtiter TM wells are washed with PBS and developed with a radiolabeled, enzyme conjugated, or otherwise labeled anti-Ig antibody.

The assay may be provided in a convenient kit containing p29 and MPO bound to microtiter TM wells (or other suitable substrates), a positive control sample (e.g., serum from a patient positively diagnosed as having pauci-immune NCGN), and other reagents needed to perform the assay. Alternatively both proteins may be bound in the same well.

The kit can also include materials for detection of anti-glomerular basement membrane (anti-GBM) antibodies. For example, collagenase digests of glomerular basement membrane can be bound to microtiter TM wells (Wilson et al., *Kidney Int.* 6:114A, 1974.

Example of A Direct Solid Phase Immunoassay for Pauci-immune NCGN Auto-antibodies A direct solid phase immunoassay was used to test the sera of four groups of individuals. Group A consisted of 42 patients with pauci-immune NCGN; group B consisted of 200 normal blood bank donors; group C consisted of 18 patients who had tested positive for anti-GBM antibodies; group D consisted of 62 patients in which a diagnosis of RPGN was considered, but who were not found to have evidence of pauci-immune NCGN or anti-GBM nephritis.

p29 and MPO Radioimmune Assay p29 was purified from crude acid extracts of isolated granulocytes by monoclonal antibody affinity chromatography as previously described (Niles et al., Blood 74:188, 1989). Purified MPO was purchased from Calbiochem (San Diego, Calif.). p29 and MPO were diluted to ten and five micrograms per milliliter respectively in borate buffered saline pH 8.1 (BBS). p29 or MPO at 35 μl/well were incubated in the wells of polyvinyl microtiter TM plates (Costar Scientific, Cambridge, Mass.) for 1 hr at 37° C. As controls, some well were incubated with BBS alone to assess non-specific binding. Unbound sites were blocked by adding 1% nonfat dried milk in BBS to the wells for 1 hr at 37° C. The wells were then incubated in triplicate with 35 μl of various dilutions of serum for 2 hours (or overnight) at room temperature. After washing with BBS, the wells were incubated with 35 ml of $^{125}$I labelled goat anti-human immunoglobulin (1.7 μg/ml at 1500 CPM/ng). After a final round of washing, the wells were dried and counted for gamma activity. Two standard positive control serum samples, one with anti-p29 activity and one with anti-MPO activity, were run in every assay at eight serial dilutions from 1:16 to 1:2048. Each test serum was assayed at a 1:16 dilution. Triplicate counts were averaged, and the average counts of each sample obtained with the control wells alone (nonspecific counts) was subtracted from the average counts obtained with p29 or MPO. Standard curves were created with the eight values from the positive controls. The two standard positive undiluted serum samples were arbitrarily assigned 128 units of activity, with each successive 1:2 dilution having one half as many units. The counts from each test serum (with nonspecific counts subtracted) were then read off the standard curve to determine the number of units of anti-p29 or anti-MPO activity.

Receiver operating characteristic curves were derived from the mean and standard deviation of the log of the titers of anti-p29 and anti-MPO antibodies for patients with pauci-immune NCGN and for the normal controls (Sox et al., *Medical Decision Making*, Butterworths, 1988). Cutoff valves were selected to give the highest possible combined sensitivity while maintaining a combined specificity of 99% for the anti-p29 and anti-MPO assays.

Results

Figure 2:
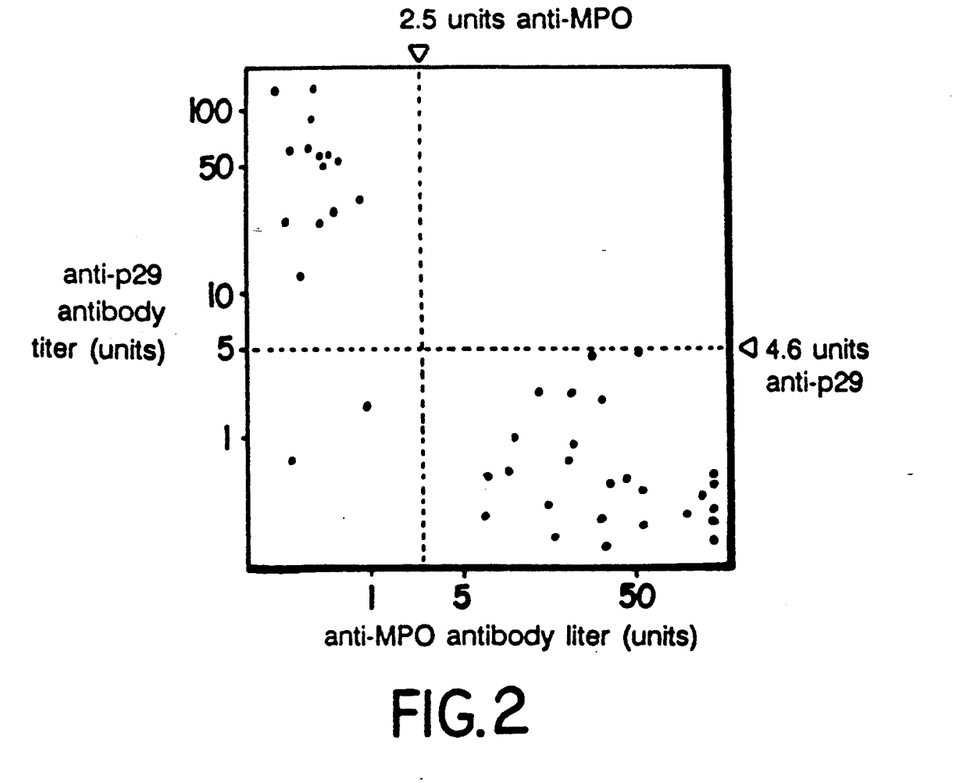
FIGS. 2-5 are representations of the results of a direct solid phase immunoassays for pauci-immune NCGN.
Figure 3:
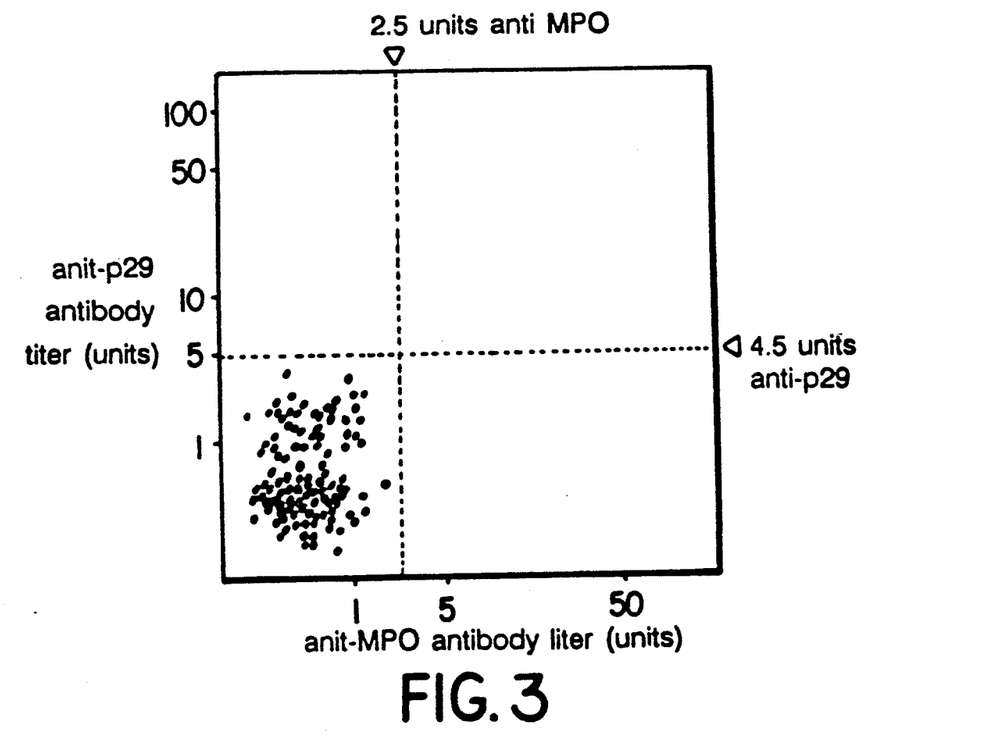

Anti-p29 and anti-MPO antibodies were scored on a scale ranging from less than 1 unit to 128 or more units of activity, as described above. Antibody titers for groups A (pauci-immune NCGN) and B (blood bank donors) are plotted in FIGS. 2 and 3 respectively. As described in the methods, using these two groups and maintaining a combined specificity of 99% for the anti-p29 and the anti-MPO assays, we estimated a combined sensitivity of 95% for pauci-immune NCGN, with cutoff values of 4.5 units for anti-p29 and 2.5 units for anti-MPO. All except two of the 42 patients in group A (pauci-immune NCGN) had positive tests either for anti-p29 or anti-MPO antibodies. One of two negative patients was found to have antibodies to p29 in a repeat serum drawn three months later; no repeat serum specimen was available from the other patient. There was only one patient who was diagnosed as having Wegener's granulomatosis whose serum did not test positive for anti-p29 antibodies; this patients serum did test positive for anti-MPO antibodies. All samples from the blood bank donors were negative for both antibodies.

The cutoff values determined above were used to analyze test results from two other groups C and D.

are: myeloperoxidase, complement C3 (Robbins, *Pathological Basis of Diseases*, Sanders, p. 1029) streptococcus antigen (Causer, *American J. Kidney Diseases* 11:449, 1988), NC1 domain of α3 chain of type IV collagen (Weislander et al., *Proc. Nat. Acad. Sci., USA* 81:1544, 1984), DNA (Condemi et al., *JAMA* 258:2920), and instructions for detecting said auto-antibodies.

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
( A ) LENGTH: 27
( B ) TYPE: amino acid
( D ) TOPOLOGY: linear ( i i ) SEQUENCE DESCRIPTION: SEQ ID NO: 1:

Ile Val Gly Gly His Glu Ala Gln Pro His Ser Arg Pro Tyr Met Ala
                  5                   10                  15

Ser Leu Gln Met Arg Gly Asn Pro Gly Ser His
              20                  25

Group C was composed of 18 patients which had tested positive for anti-GBM antibodies. The immunofluorescence findings for these patients were characteristic of anti-GBM nephritis. Group D consisted of 62 patients in which a diagnosis of RPGN was considered, but who were not found to have evidence of pauci-immune NCGN or anti-GBM nephritis.

Figure 4:
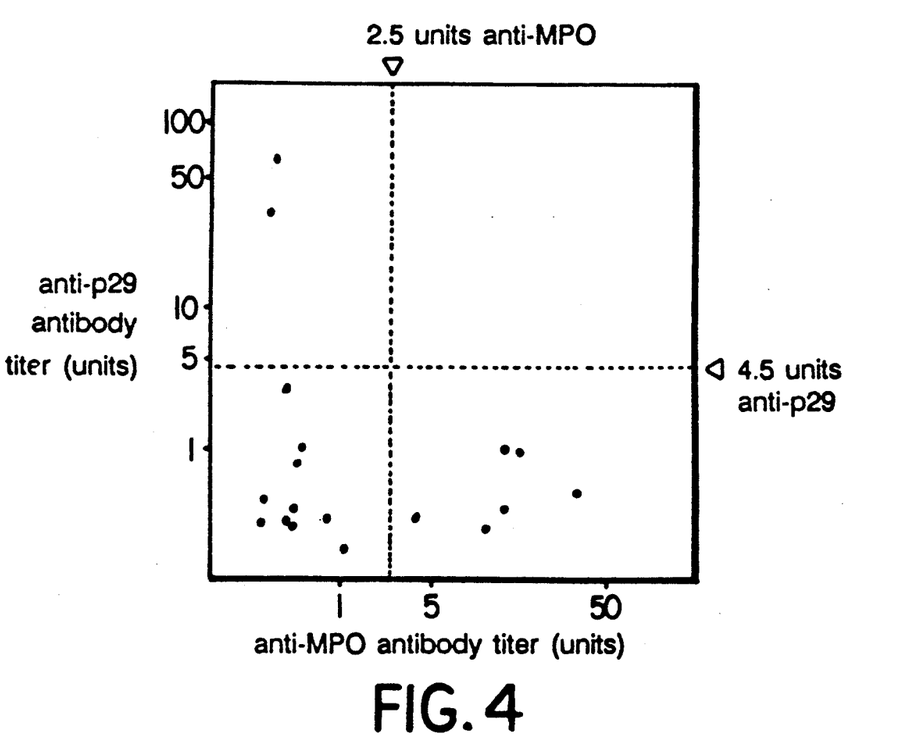
Figure 5:
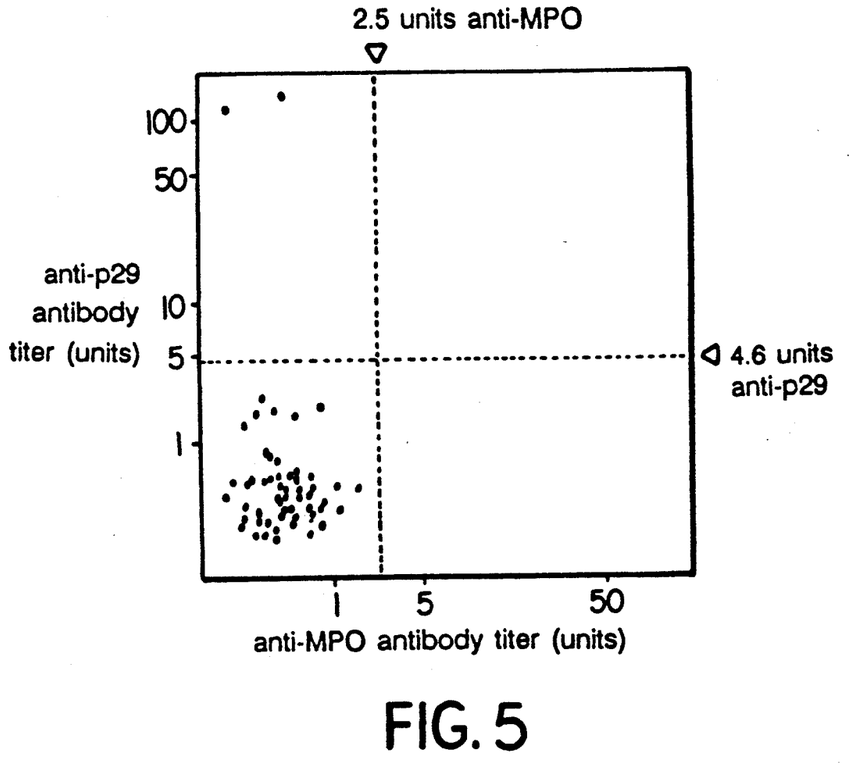

Among the 18 patients in group C two were found to have anti-p29 antibodies and six were found to have anti-MPO antibodies (FIG. 4). In group D, two of the 62 patients scored positively, both for anti-p29 antibodies (FIG. 5). On review of available clinical and laboratory data, it was concluded that these two patients had NCGN.

Overall, among patients with the clinical syndrome of RPGN, a positive test for anti-p29 or anti-MPO combined with a negative test for anti-GBM antibodies provided a highly reliable guide to the diagnosis of pauci-immune NCGN even in the absence of a kidney biopsy.

Use

The p29 protein and/or antibodies against p29 can be used to test for the presence of the auto-antibodies diagnostic for Wegener's granulomatosis. In combination with myeloperoxidase and/or antibodies against myeloperoxidase, p29 and/or antibodies against p29 can be used to test for the presence of the auto-antibodies diagnostic for pauci-immune NCGN. The p29 protein can be used in combination with other antigens to test for the presence of antibodies associated with glomerulonephritis.

Other Embodiments

Other embodiments are within the following claims. For example, p29 and or antibodies against p29 can be used as part of a kit, employing a direct or an indirect immune assay, to detect antibodies associated with any of a broad spectrum of conditions associated with glomerulonephritis. The antigens which could be included

We claim:

1. A method of diagnosing pauci-immune necrotizing and/or crescentic glomerulonephritis in a patient, said method comprising:
   (a) contacting a sample of biological fluid from said patient with a substantially pure protein having the following characteristics:
   (i) it can be isolated from neutrophils;
   (ii) it has a mass of approximately 29 kD as determined by SDS-PAGE;
   (iii) it is capable of binding diisopropylfluorophosphate;
   (iv) it has a pI of approximately 9.2–9.4;
   (v) it is capable of binding to auto-antibodies present in the sera of individuals afflicted with Wegener's granulomatosis; and
   (vi) it has the N terminal amino acid sequence Ile-Val-Gly-Gly-His-Glu-Ala-Gln-Pro-His-Ser-Arg-Pro-Tyr-Met-Ala-Ser-Leu-Gln-Met-Arg-Gly-Asn-Pro-Gly-Ser-His (SEQ. ID NO.: 1); and
   (b) detecting immune complexes formed in step (a), formation of said immune complexes being diagnostic of pauci-immune necrotizing and/or crescentic glomerulonephritis.

2. The method of claim 1, further comprising contacting a sample of biological fluid from said patient with myeloperoxidase; and detecting immune complexes, formation of said immune complexes being diagnostic of pauci-immune necrotizing and/or crescentic glomerulonephritis.

3. A method of diagnosing pauci-immune necrotizing and/or crescentic glomerulonephritis in a patient, said method comprising:
   (a) providing an immune complex of a protein having the following characteristics:
   (i) it can be isolated from neutrophils,
   (ii) it has a mass of approximately 29 kD as determined by SDS-PAGE, (iii) it is capable of binding diisopropylfluorophosphate,
(iv) it has a pI of approximately 9.2–9.4,
(v) it is capable of binding to auto-antibodies present in the sera of individuals afflicted with Wegener's granulomatosis, and
(vi) it has the N terminal amino acid sequence Ile-Val-Gly-Gly-His-Glu-Ala-Gln-Pro-His-Ser-Arg-Pro-Tyr-Met-Ala-Ser-Leu-Gln-Met-Arg-Gly-Asn-Pro-Gly-Ser-His (SEQ. ID NO.: 1); and a monoclonal antibody directed against said protein;

(b) contacting said immune complex of step (a) with a sample of biological fluid from said patient; and (c) detecting the binding of auto-antibodies in said sample to said immune complexes of step (a), binding of said auto-antibodies to said immune complexes being diagnostic of pauci-immune necrotizing and/or crescentic glomerulonephritis.

4. The method of claim 3, further comprising providing an immune complex of myeloperoxidase and a monoclonal antibody directed against myeloperoxidase; contacting said immune complex with a sample of biological fluid from said patient; and detecting the binding of auto-antibodies in said sample to said immune complexes, binding of said auto-antibodies to said immune complexes being diagnostic of pauci-immune necrotizing and/or crescentic glomerulonephritis.

5. A diagnostic kit for diagnosing pauci-immune necrotizing and/or crescentic glomerulonephritis, comprising a substantially pure protein having the following characteristics:
(i) it can be isolated from neutrophils;
(ii) it has a mass of approximately 29 kD as determined by SDS-PAGE;
(iii) it is capable of binding diisopropylfluorophosphate;
(iv) it has a pI of approximately 9.2–9.4;
(v) it is capable of binding to auto-antibodies present in the sera of individuals afflicted with Wegener's granulomatosis; and
(vi) it has the N terminal amino acid sequence Ile-Val-Gly-Gly-His-Glu-Ala-Gln-Pro-His-Ser-Arg-Pro-Tyr-Met-Ala-Ser-Leu-Gln-Met-Arg-Gly-Asn-Pro-Gly-Ser-His (SEQ. ID NO.: 1).

6. The diagnostic kit of claim 5, further comprising myeloperoxidase.

7. A diagnostic kit for diagnosing pauci-immune necrotizing and/or crescentic glomerulonephritis, comprising:
(a) a substantially pure protein having the following characteristics:
(i) it can be isolated from neutrophils,
(ii) it has a mass of approximately 29 kD as determined by SDS-PAGE,
(iii) it is capable of binding diisopropylfluorophosphate,
(iv) it has a pI of approximately 9.2–9.4;
(v) it is capable of binding to auto-antibodies present in the sera of individuals afflicted with Wegener's granulomatosis, and
(vi) it has the N terminal amino acid sequence Ile-Val-Gly-Gly-His-Glu-Ala-Gln-Pro-His-Ser-Arg-Pro-Tyr-Met-Ala-Ser-Leu-Gln-Met-Arg-Gly-Asn-Pro-Gly-Ser-His (SEQ. ID NO.: 1); and (b) a monoclonal antibody directed against the protein of (a).

8. The diagnostic kit of claim 7, further comprising myeloperoxidase; and a monoclonal antibody directed against myeloperoxidase.

9. A diagnostic kit, comprising:
(a) myeloperoxidase;
(b) complement C3;
(c) streptococcus antigen;
(d) NC1 domain of α3 chain of type IV collagen;
(e) DNA; and
(f) a substantially pure protein having the following characteristics:
(i) it can be isolated from neutrophils,
(ii) it has a mass of approximately 29 kD as determined by SDS-PAGE,
(iii) it is capable of binding diisopropylfluorophosphate,
(iv) it has a pI of approximately 9.2–9.4,
(v) it is capable of binding to auto-antibodies present in the sera of individuals afflicted with Wegener's granulomatosis, and
(vi) it has the N terminal amino acid sequence Ile-Val-Gly-Gly-His-Glu-Ala-Gln-Pro-His-Ser-Arg-Pro-Tyr-Met-Ala-Ser-Leu-Gln-Met-Arg-Gly-Asn-Pro-Gly-Ser-His (SEQ. ID NO.: 1).

* * * * *

UNITED STATES PATENT AND TRADEMARK OFFICE
CERTIFICATE OF CORRECTION

PATENT NO. : 5,200,319
DATED : April 6, 1993
INVENTOR(S) : M. Amin Arnaout, et al It is certified that error appears in the above-indentified patent and that said Letters Patent is hereby corrected as shown below:

On the Title Page, Item [56], "OTHER PUBLICATIONS": add
--Niles et al., Blood, 74:1888, 1989--.

Signed and Sealed this

Nineteenth Day of April, 1994

Attest:

BRUCE LEHMAN

Attesting Officer   Commissioner of Patents and Trademarks